United States Patent
Llamido (10) Patent No.: US 10,613,030 B2
(45) Date of Patent: Apr. 7, 2020

(54) SYSTEM FOR BACTERIA SCANNING AND HAND SANITIZATION

(71) Applicant: Maria Victoria Llamido, Union City, CA (US)

(72) Inventor: Maria Victoria Llamido, Union City, CA (US)

(73) Assignee: Maria Victoria Llamido, Union City, CA (US)

( * ) Notice: Subject to any disclaimer, the term of this patent is extended or adjusted under 35 U.S.C. 154(b) by 0 days.

(21) Appl. No.: 15/588,593

(22) Filed: May 6, 2017

(65) Prior Publication Data
US 2018/0321153 A1     Nov. 8, 2018

(51) Int. Cl.
*G01N 21/64*     (2006.01)
*A61L 2/24*     (2006.01)
*A61L 2/00*     (2006.01)

(52) U.S. Cl.
CPC ........ *G01N 21/6447* (2013.01); *A61L 2/0088* (2013.01); *A61L 2/24* (2013.01); *G01N 21/6428* (2013.01); *A61L 2202/11* (2013.01); *A61L 2202/14* (2013.01); *G01N 2201/061* (2013.01)

(58) Field of Classification Search
CPC ........... G01N 21/6447; G01N 21/6428; G01N 2201/061; A61L 2/0088; A61L 2/24; A61L 2202/14; A61L 2202/11
See application file for complete search history.

(56) References Cited

U.S. PATENT DOCUMENTS

2017/0073722 A1*   3/2017   Kanhye .................... C12Q 1/04

* cited by examiner

*Primary Examiner* — Michael C Bryant (57) ABSTRACT

This disclosure relates generally to a systems and method provided for monitoring bacteria and germs on users' hands, and further providing solutions to determine compliance with hand hygiene guidelines. The system is embedded with a volatile technology to show bacteria on hands after hand washing. The system comes with a sensor depicting the need to wash hands again, or requirement for use of sanitizer. The sanitizing machine is also part of the main system, which sanitizes all bacteria areas being focused on, and also has a hand drying facility. The system can be placed and installed near any hand washing area and is equally good for use in households and commercial avenues, especially in the health and food industry.

45 Claims, 3 Drawing Sheets

SYSTEM FOR BACTERIA SCANNING AND HAND SANITIZATION

BACKGROUND

Field of the Invention

The present invention relates to bacteria scanning and hand sanitization. The field is closely related to the hygiene and health industry, and indirectly related to the medical field. The invention is a machine that will censor (eliminate), and detect, bacteria on hands through sensors. For hygiene care, such machines are in place, but these machines not designed for everyday use. The present machine is designed for everyday use.

Aspects of the present invention relate more particularly to daily hygiene care at home, schools, clinics, hospitals and businesses, with the present invention used as a normal daily routine appliance. This invention will have more focus on household uses, and the youth. This is a critical health and infection prevention device, invented based on the concept of "Prevention is better than Cure".

Description of the Related Art

As mentioned above, the invention is directly related to hygiene and health industry but not only limited to these industries. The invention is based on the concept that prevention is better than cure. A large number of people die each year from infections acquired in hospitals. In the same context, infections and germs are transferred mainly from hands to other people, food items and, most critically, the mouth. All of this results in multiple diseases, deaths, pain factor and costs, and burden on the medical and health industry. It has been estimated that as many as one hospital patient in ten, or 2 million patients a year, acquires a nosocomial infection in the United States alone. Estimates of annual costs related to nosocomial infection range from $4.5 billion to $11 billion and up. Studies have shown that at least one third of nosocomial infections are preventable. Nosocomial infections due to resistant organisms are an extremely serious problem that threatens the U.S. healthcare system and the welfare of American citizens. Microbes can acquire resistance to antibiotics and antifungal and antiviral agents and as the numbers of resistant organisms increase, the number of new antimicrobial agents to treat them has not kept pace.

It has been reported that more than 50% of all nosocomial infections can be directly related to the transmission of harmful bacteria by healthcare workers who have not properly washed their hands before and after each patient contact. Thus, the best means to prevent transfer of these organisms from patient to patient and to reduce the emergence of resistant organisms is hand washing with soap and water between patient contacts. In the same context, children at home, and children in schools, do not care for this factor and the germs are transferred to their internal system causing different diseases. In the food industry, as well, the highest level of pure hygiene is not achieved, as people, owner and managers are not aware of the fact that even after washing many bacteria and germs are still in contact with their hands.

There are many possible reasons for non-compliance with recommended hand washing practices. For example, there may not be sufficient time to properly wash hands, or wash stations may be placed in inconvenient locations. Some people simply forget to wash their hands. Others may not realize how infrequently or inadequately they comply with recommended hand washing practices. Others still may not fully understand the benefits of hand washing. Some or all of these issues may be addressed if means were provided to monitor compliance with recommended hand washing practices.

The invention is a bacteria-free censoring machine. The invention will reveal a full view of all the specific locations where bacteria is residing on the user's hands, utilizing a colored light. Once bacteria traces are detected, the sensor will indicate the condition to the user. The user would then be presented with an indication. The indication would have 02 options or recommendations for the user. The first would be to properly wash hands again or to push a button, which will cause a sanitizing liquid agent to be sprayed on both hands targeting the bacteria's location, as well as automatically drying user's hands.

This is a critical health and infection prevention device innovation that will prevent the obtaining and spreading of dangerous infectious diseases for health workers, their patients, food services, and in any other critical situation where hand sanitation is paramount.

The new innovation, which is a Bacteria Hands Free Censoring Machine would ensure that bacteria will not be transferred from one patient to another, or from patients to health care professionals, without the transferee knowing. In the same context, the utility of this invention is very important from other industrial fields like restaurant industry, food preparation, hospitals, students, schools and the household.

This is not the first invention in the world related to bacteria scanning machines. Part of the uniqueness of this invention lies in the additional sensor suggesting washing of hands or process of sanitization with drying of hands. However, to Applicant's knowledge, a machine and invention with similar capabilities is not currently available. It is to such a system that the present invention is directed.

SUMMARY

The following term numbers shall refer to different parts of the invention. (1) Case. (2) Power Cord. (3) Viewing screen. (4) On/off switch. (5) Automatic touch control switch. (6) Button that can dispense sanitizing fluid. (7) Hand and wrist ports. (8). USB port.

In light of the disadvantages of the prior art, the following summary is provided to facilitate an understanding of some of the innovative features unique to the present invention, and this summary is not intended to be a full description. A full appreciation of the various aspects of the invention can be gained by taking the entire specification, claims, drawings, and abstract as a whole into account.

The primary object of the invention is related to provide a systems and method for monitoring and promoting hand hygiene practices. According to the subject invention, a system for promoting adherence to hand washing (or hygiene) guidelines comprises a hand washing agent that includes a bacteria detectable scanner with a sensor to suggest further action for pure hygiene. The system would either advise a user to wash hands again or give an option to sanitize hands through the same system and dry the hands.

Hibiclens is one example of a hand sanitizer, which the system can place on a user's hands after the system informs the user that bacteria are present on his or her hands, and the user consents to having sanitizer placed on his or her hands.

The invention should be effective when any commercially available hand sanitizer or commercially available soap solution, or commercially available rubbing alcohol, is placed on the user's hands after the system informs the user that bacteria are present on his or her hands, and the user consents to having sanitizer placed on his or her hands.

The invention can also be used with any commercially available hand sanitizer, soap solution, or commercially available rubbing alcohol, in embodiments when the system detects bacteria on the user's hands, and informs the user of this, but the actual process of the user washing his or her hands afterwards is carried out by a different system.

The system comprises a volatile or semi-volatile system, also referred to as a "Bacteria Hands Free Censoring Machine" which comes with a sensor-based detector to censor and show the bacteria and germs on the hand. The Bacteria Hands Free Censoring Machine also comprises a sanitizing chemical to sanitize hands, if required. The invention has another unique feature of suggesting the option of washing the hands again, or getting the hands sanitized through the machine, with focused sanitization on the bacteria-filled area of the hand.

This Summary is provided merely for purposes of summarizing some example embodiments, to provide a basic understanding of some aspects of the subject matter described herein. Accordingly, it will be appreciated that the above-described features are merely examples and should not be construed to narrow the scope or spirit of the subject matter described herein in any way. Other features, aspects, and advantages of the subject matter described herein will become apparent from the following Detailed Description, Figures, and Claims.

Some Bacteria that the Machine Can Detect

The machine of the present invention can presently detect many species of bacteria that are harmful to humans. The machine can detect these bacteria by detecting the fluorescence created by the combination of the polymer PNIPAM and the antibiotic vancomycin that adheres to the bacteria, when ultraviolet light is shone on the bacteria. Some embodiments of the machine can also detect the fluorescence created directly by the bacteria when ultraviolet light is shone on the bacteria.

Shigella infection (shigellosis) is an intestinal disease caused by a family of bacteria known as shigella. The main sign of shigella infection is diarrhea, which often is bloody. Shigella can be passed through direct contact with the bacteria in the stool. For example, this can happen in a childcare setting when staff members don't wash their hands well enough after changing diapers or helping toddlers with toilet training. Shigella bacteria also can be passed in contaminated food or by drinking or swimming in contaminated water.

Children between the ages of 2 and 4 are most likely to get shigella infection. A mild case usually clears up on its own within a week. When treatment is needed, doctors generally prescribe antibiotics. Infection occurs when a person accidentally swallows shigella bacteria.

A person can accidentally swallow shigella bacteria when they touch their mouth, eat contaminated food, swallow contaminated water, live in group housing or engage in group activities, or live or travel in areas that lack adequate sanitation.

The machine of the present invention detects shigella bacteria in the manners discussed above.

Salmonella is another type of bacteria that is dangerous to humans. The machine of the present invention detects salmonella bacteria in the manner discussed above.

The machine of the present invention can also be used with other chemicals, where using the following steps 1. Spraying a mist containing the relevant chemical, or combination of chemicals, upon the user's hands, when they are placed into the machine. The chemical or combination of chemicals must be of a type that adheres to bacteria and fluoresces in ultraviolet light.

Use of the Machine to Prevent Outbreaks of Contamination

The present invention includes a USB port, which can be connected to a computer, to transmit data electronically. Some embodiments of the machine include other methods of electronically connecting the machine to a computer. The computer can then be electronically connected to other computers, on the internet.

The machine of the present invention can be attached to a computer to provide certification, proof that hand washing, hand sanitizing and bacterial screening have been conducted before performing surgeries and handling food products. A hospital, restaurant, school, or other business can then keep a log of such certifications, for insurance purposes or other purposes.

A computer or group of related computers can use data collected from the machines of the present invention to learn how many individuals are currently contaminated by Shigella and Salmonella bacteria, to prevent the wide spread of bacteria and accurately locate the sources.

A large group of computers, operating over the internet, can potentially monitor the spread of bacterial contamination by sending, to each other, the information that the computers have acquired from the machines of the present invention that are attached to these computers. This presents the possibility of monitoring the spread of bacterial contamination between people in real time. In this way, the present system can be used to locate and stop potential outbreaks of food-borne illness quickly. The system including a large number of computers connected to machines of the present invention can create a report, and can display the report locally, or mail the report over the internet, when a large number of people appear to be contaminated with a type of bacteria within a short period of time. The present system can also be very useful for stopping outbreaks of bacteria-borne disease among children at schools.

Some of the Principles Governing Ultraviolet Detection of Bacteria

Researchers have developed polymers that fluoresce in the presence of bacteria, paving the way for the rapid defection and assessment of wound infection using ultraviolet light.

When contained in a gel and applied to a wound, the level of fluorescence detected will alert clinicians to the severity of infection. The polymers are irreversibly attached to fragments of antibiotics, which bind to either gram negative or gram positive bacteria—both of which cause very serious infections—informing clinicians as to whether to use antibiotics or not, and the most appropriate type of antibiotic treatment to prescribe. The team also found that they could use the same gels to remove the bacteria from infected wounds in tissue engineered human skin.

Professor Sheila MacNeil, an expert in tissue engineering and wound healing, explained: "The polymers incorporate a fluorescent dye and are engineered to recognize and attach to bacteria, collapsing around them as they do so. This change in polymer shape generates a fluorescent signal that we've been able to detect using a hand-held UV lamp."

Research has already demonstrated that the polymer (PNIPAM), modified with an antibiotic (vancomycin) and containing a fluorescent dye (ethidium bromide), shows a clear fluorescent signal when it encounters gram negative bacteria. Other polymers have been shown to respond to *S. aureus*, a gram positive bacteria. These advances mean that a hand-held sensor device can now be developed to be used in a clinical setting. The present invention is one such device.

Therefore, some embodiments of the machine of the present invention includes a sprayer, which will spray a mist containing a combination of PNIPAM and vancomycin on the user's hands, when they are placed inside the machine. The combination of PNIPAM and vancomycin will then stick to any bacteria on the user's hands. The machine will shine ultraviolet light upon the user's hands, and the bacteria on the hands will emit light of another wavelength. This light will be detected by the viewing screen, and the viewer will be able to visually tell whether there are any bacteria on his or her hands.

The light emitted by the machine will be below the "limit values" for that kind of light. Lower-wavelength light has dramatically lower relative spectral effect.

Some embodiments of this device would also include a purple or blue light, which would flash on the user's hands. This would cause the bacteria on the user's hands to fluoresce. This, in turn, would allow the user to visibly see the location of the bacteria residing on her hands.

Some Examples of the Use of the Machine

The machine can be designed to emit ultraviolet light at levels that are not substantially harmful to humans. Scientists have created charts of the amount of ultraviolet radiation of different wavelengths that is harmful to humans. Ultraviolet light of some wavelengths is much less harmful than ultraviolet light of other wavelengths. Bacteria, however, will fluoresce when ultraviolet light of any kind is shone upon them. Furthermore, the combination including vasomycin will fluoresce when any kind of ultraviolet light is shone upon it.

Therefore, most embodiments of the machine can emit ultraviolet light between the wavelengths of 255 and 340 nm, which are less harmful to humans, but which cause the bacteria to fluoresce using the methods described herein.

When the user places his hands into the machine, the machine will shine ultraviolet light on the user's hands, and will detect any bacteria that might exist. In most embodiments of the invention, the machine will contain a processor that will contain a computer program.

The computer program will analyze the fluorescent pattern on the user's hands to determine the amount of bacteria on the user's hands. Embodiments of the machine have a mapping mechanism or a circuit grid to measure the bacterial density on the top and bottom of hands, and to calculate the bacteria percentage. This mapping mechanism or circuit grid will be connected to the processor containing the computer program, and will give input to the computer program, concerning the parts of the user's hands that are fluorescing.

Once bacteria traces are still detected on the user's hands, the program will give the user two recommendations to either: Properly wash the user's hands again or to push a button to where a sanitizing liquid agent will be sprayed on both hands targeting the bacteria location. The machine will then automatically dry the hands from top and bottom area. The machine can give these recommendations by voice.

The machine will then monitor the bacteria on the surface of the hands, in the manner described above, again. The machine will then either verify that both hands are 100% clean or bacteria free, or inform the user that she needs to properly wash her hands again or spray sanitizing liquid on the hands in the manner described above.

The machine in most embodiments, will have a light, such as a green light, that will flash and inform the user that his or her hands are adequately clean.

It is expected that the machine will be able to detect the bacteria in less than 5 seconds, and provide the percentage of bacteria traces on hands after another 5 seconds.

Some of the primary components of the machine will be the stainless steel case, which the (2) Power Cord will be connected to. The (3) Viewing screen and (4) On/off switch and (5) Automatic touch control switch and (6) Button that can dispense sanitizing fluid and (8) USB port will all be part of the case. The (7) Hand and wrist ports will be large holes in the case that the user can stick her hands into.

One Embodiment of the Program Inside the Machine

In one embodiment of the program inside the machine, there will be the following criteria (percentages refer to the percentage of the surface of the hands that are free of bacteria).

Program Criteria:
- 100%-80%—passed as cleaned and sanitized; the blue light or UV-light reflector shouldn't have any traces of bacteria on both hands.
- 70%-60%—mild and needed to spray alcohol based sanitizer, no need to wash hands or optional to the user if prefer to wash hands again to obtain 80%-100% results.
- 60%—below-not acceptable, need to rewashed hands, focusing on the area to where the bacteria were visible to UV lights. Redo the process, screen hands again and sanitized until achieve 80%-100% results.
- Using concentration of alcohol between 60-95% are more effective at killing germs.

Some embodiments of the machine have their own self-cleaning mechanisms, after being used to achieve accurate results for the next users.

BRIEF DESCRIPTION OF THE DRAWINGS

The accompanying figures, where like reference numerals refer to identical or functionally similar elements throughout the separate views, together with the detailed description below, are incorporated in, and form part of, the specification, and serve to further illustrate embodiments of concepts that include the claimed invention, and explain various principles and advantages of those embodiments.

Figure 1:
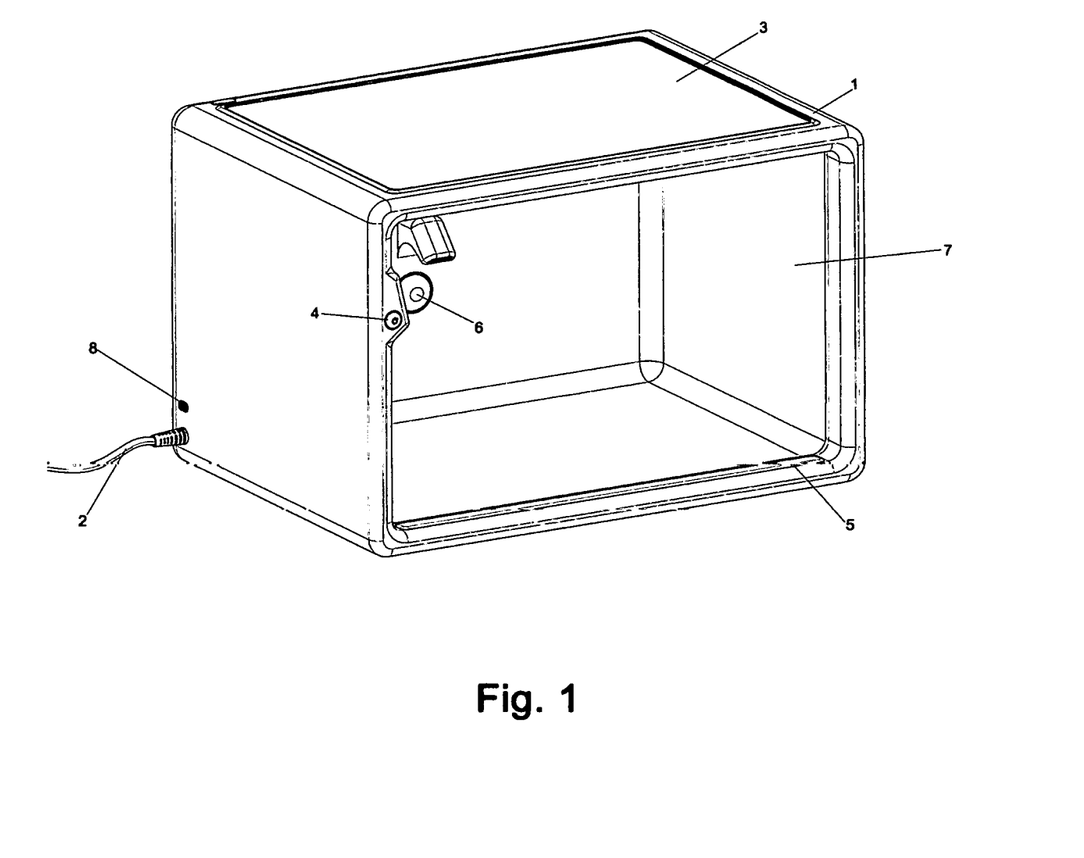
FIG. 1 shows the user interface of one of the systems, with full utility. It clearly shows how hands would be put in the machine for bacterial censoring. The diagram also indicates the areas with bacteria on hand and the need for re-wash or sanitization. The case and screen are clearly visible. The power cord and USB can be seen.
Figure 2:
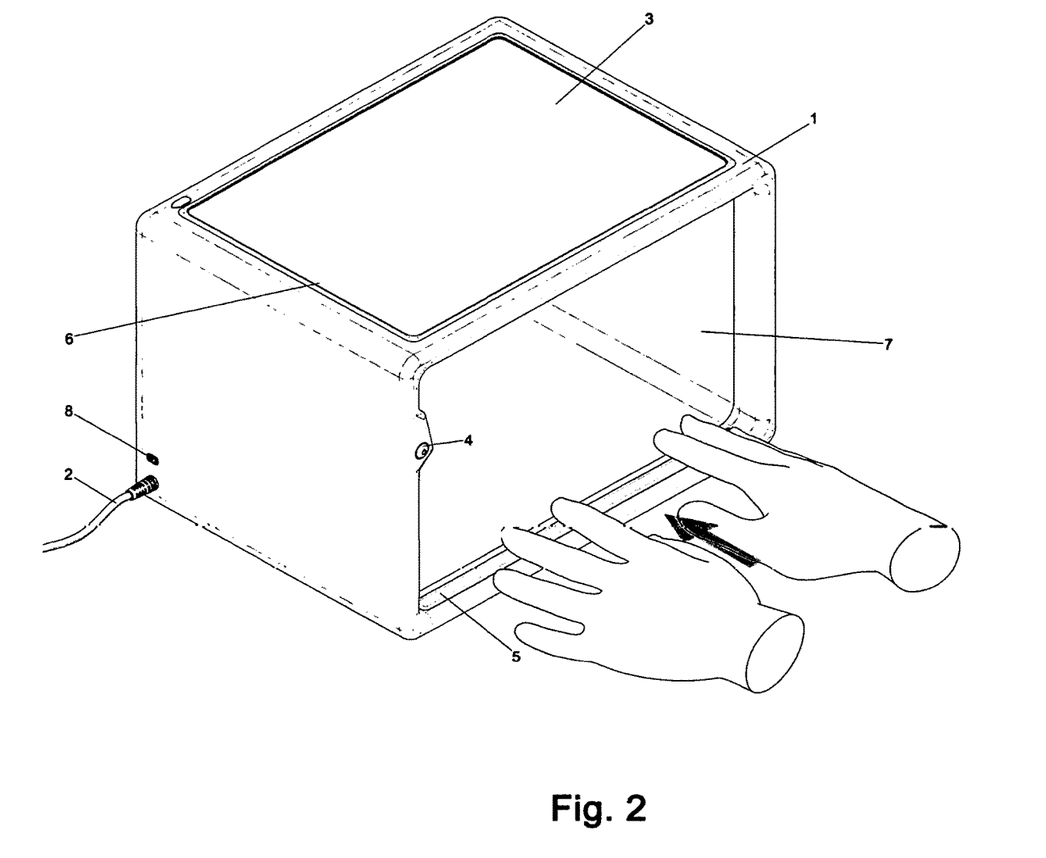
FIG. 2 shows the side view of a machine system, giving the aerial view. It also shows the spacing for hand testing. The Sensor screen and the upper volatile surface show the results.
Figure 3:
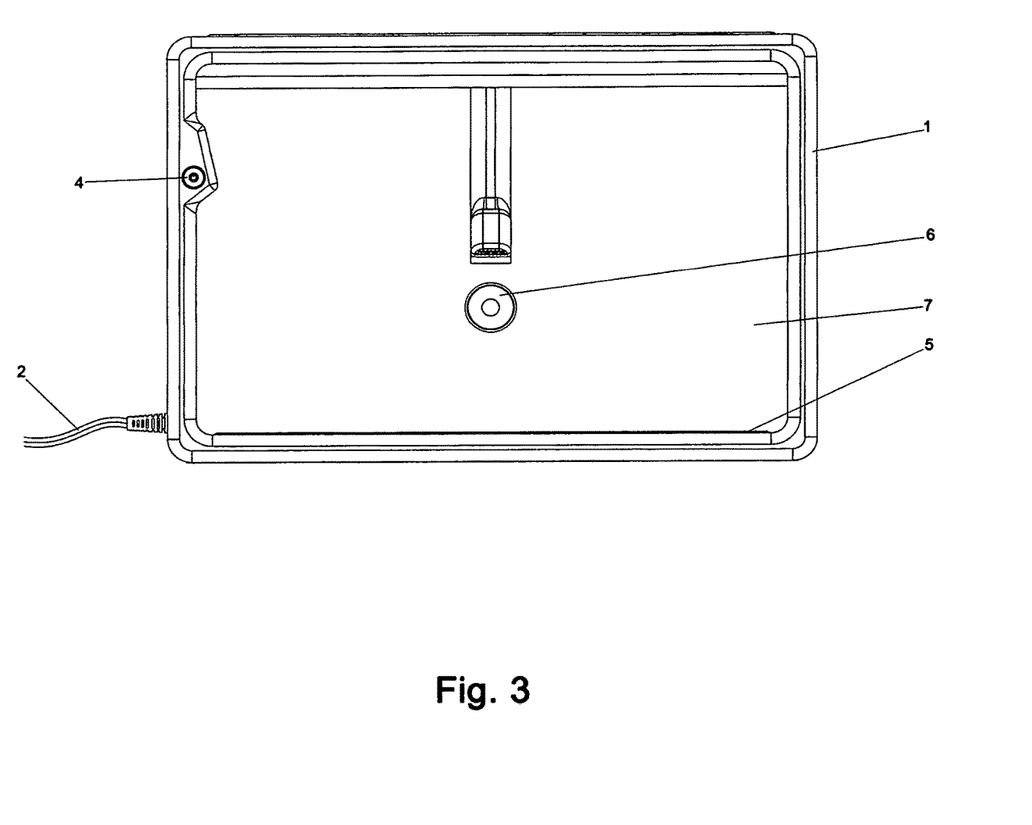
FIG. 3 shows a side view while the system is in the rendering process and ready for use. The side LED indicators show the activity lights. The sensors are built into the system. The sensors measure the bacteria on the user's hands, and then communicate the need for re-wash of hands or sanitization.

Skilled artisans will appreciate that elements in the figures are illustrated for simplicity and clarity, and have not necessarily been drawn to scale. For example, the dimensions of some of the elements in the figures may be exaggerated relative to other elements to help to improve a viewer's understanding of embodiments of the present invention.

The apparatus and method components have been represented, where appropriate, by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

The present invention provides a system to detect bacteria and germs on the hands with the aim to ensure users' compliance in hand hygiene activities. In one preferred embodiment, the "Bacteria Hands Free Censoring Machine" is a machine used for censoring and scanning bacteria on the hands, with a sanitizing compound that is inconspicuous, so that when a subject applies the hand washing sanitizer to one's hands, the "Bacteria Hands Free Censoring Machine" is essentially undetectable to the subject's olfactory senses during and after the hand washing event. More preferably, when appropriate, the "Bacteria Hands Free Censoring Machine" also suggests the subject should engage in sanitization or hand wash again, where if sanitized the hands are dried out as well.

In operation of an embodiment, a subject (e.g., a healthcare provider, school children, a household, or an employee of a restaurant) is provided with a detector, the Bacteria censoring machine during work hours, or even at different times in homes. The scanner is designed to remind or alert the subject (or other interested parties, such as a monitoring agent, a customer, or a patient) regarding whether the subject has washed his/her hands properly, or whether the subject requires another hand wash. In the same context, this embodiment also gives a provision of hand sanitization. The censor machine can be positioned in close proximity to a hand washing station, including a sink with exogenous (e.g., tap) water-requiring hand washing media (e.g., soap and water, Hibiclens) or the site of non-exogenous water requiring hand washing media (e.g., gel or foam hand washing agents). The detector contains the necessary sensor to detect the bacteria as well as an indicator to receive and communicate information from the sensor. After a hand washing event, bacteria and germs from the hand-washing agent are detected on the subject's hands, or emanating from, the subject's hands, using the sensor. If the germs are detected, the indicator will communicate detection of the compound constituting the germs, which is a sign of subject performance in hand washing. The same system will provide hand sanitization options, or will suggest washing hands again.

While a specific embodiment has been shown and described, many variations are possible. With time, additional features may be employed. The particular shape or configuration of the platform, or the interior configuration, may be changed to suit the system or equipment with which it is used.

Having described the invention in detail, those skilled in the art will appreciate that modifications may be made to the invention without departing from its spirit. Therefore, it is not intended that the scope of the invention be limited to the specific embodiment illustrated and described. Rather, it is intended that the scope of this invention be determined by the appended claims and their equivalents.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The invention claimed is:

1. An apparatus for detecting bacteria on a user's hands, said apparatus comprising the following components:
   a means of providing electrical power,
   an electrically powered ultraviolet light emitter,
   a screen, and a case wherein said means of providing electrical power provides electrical power to said ultraviolet light emitter and
   wherein said case comprises an interior space and at least one opening through which a user may place at least one hand into said interior space;
   wherein said case comprises that said screen is positioned between said interior space and the outside of said apparatus such that, when a user's hand is placed into said interior space, an image of said at least one hand is seen on said screen and viewed from outside said apparatus;
   wherein said ultraviolet light emitter emits, into said interior space, ultraviolet light where the intensity of each wavelength of said ultraviolet light is below the limit value for said wavelength for the amount of time that said ultraviolet light emitter emits ultraviolet light,
   where the definition of the said limit value for any wavelength of ultraviolet light, for any defined period of time, includes the safe limit value for a year multiplied by the fraction of a year encompassed by said period of time; and
   wherein the hand fluoresces in response to the ultraviolet light and bacteria is detected through the different fluorescence of areas of the hand with and without bacteria.

2. The apparatus of claim 1, further including a processor that responds to information created by fluorescence of a user's at least one hand when the user inserts said at least one hand into said interior space through said at least one opening in said case.

3. The apparatus of claim 2 where said processor is programmed to determine the proportion of the surface area contaminated by bacteria of any of the user's hands inserted into said interior space.

4. The apparatus of claim 2 where said screen is an electronic screen, said apparatus includes a camera that captures said image of said at least one hand, and where the electronic screen displays the captured image.

5. The apparatus of claim 4, where said processor is programmed to determine, regarding a user's hand that has been inserted into said interior space, the areas of said hand that are, relative to other areas of said hand, brightly fluorescing due to the presence of bacteria the areas of said hand that are, relative to other areas of said hand, dimly fluorescing due to the lack of bacteria, the percentage of the total surface area of said hand that is, relative to other areas of said hand, brightly fluorescing; the percentage of the total surface area of said hand that is, relative to other areas of said hand, dimly fluorescing; and said processor is programmed to report the level of bacterial contamination to the user in response to the areas of said at least one hand that are relatively brightly fluorescing, the areas that are relatively dimly fluorescing, the percentage of the area of the hand that is brightly fluorescing, and the percentage of the area of the hand that is dimly fluorescing.

6. The apparatus of claim 4 further comprising one of the following items:
    a. a circuit grid, projecting a series of gridlines onto said at least one hand when said at least one hand has been inserted into said interior space, in order to subdivide said captured image where said circuit grid is operatively connected to said processor that determines the percentage of subdivisions that are contaminated by bacteria by referencing the locations and fluorescence of all said subdivisions;
    b. a mapping function with which said processor is capable of creating virtual maps of the fluorescence of said at least one hand, when said hand has been inserted into said interior space, and the processor determines the regions of said at least one hand that is contaminated by bacteria by referencing said mapped fluorescence.

7. The apparatus of claim 1 further including a means of dispensing a detecting chemical mixture onto the user's at least one hand, where said detecting chemical mixture fluoresces in ultraviolet light or visible light or both ultraviolet and visible light and fluoresces more strongly when exposed to said light and to bacteria.

8. The device of claim 7 where said sterile substance is a combination of PNIPAM and vancomycin.

9. The apparatus of claim 7, where said detecting chemical mixture is a combination of PNIPAM and vancomycin.

10. The apparatus of claim 1 where said screen is a transparent window through which a user may view items in said interior space.

11. The apparatus of claim 1 where said ultraviolet light emitter emits ultraviolet light with wavelengths of between 255 and 240 nm.

12. The apparatus of claim 2 further comprising a component that transfers data and is capable of transferring said information created by fluorescence of said at least one hand from said processor to one or more receivers located remotely from said apparatus.

13. The apparatus of claim 12 adapted into a system to monitor the spread of bacterial contamination where said system includes least two of the apparatus at known locations, and the system monitors the spread of bacterial contamination in response to the information created by hand fluorescence, transferred by the at least two apparatus, and to the locations of the at least two apparatus.

14. A method for detecting bacteria on a user's hands, said method comprising the steps of:
    (a) providing an apparatus including the following components:
        an electrical power source, an electrically powered ultraviolet light emitter, a screen, and a case where:
            the electrical power source provides electrical power to the ultraviolet light emitter;
            the case comprises an interior space, the screen, and at least one opening into the interior space through which the user may place at least one hand into the interior space; and
            the screen is positioned so that, when the at least one hand is placed into said interior space, an image of the at least one hand is seen on the screen; and
        where the ultraviolet light emitter emits ultraviolet light into the interior space where the intensity of the ultraviolet light at each wavelength emitted by said ultraviolet light emitter is below the safe limit value for said wavelength for the amount of time that said ultraviolet light emitter emits ultraviolet light, and the determination of the safe limit value for any wavelength of the ultraviolet light, for any defined period of time, includes the safe limit value for a year multiplied by the fraction of a year encompassed by said period of time;
    (b) the user inserting the at least one hand through the at least one opening into said interior space;
    (c) the ultraviolet light emitter emitting ultraviolet light upon the at least one hand and the at least one hand fluorescing in the presence of bacteria and the ultraviolet light;
    (d) the screen presenting an image responsive to the fluorescing of the at least one hand; and
    (e) the user detecting bacteria on the at least one hand by viewing the image presented by the screen.

15. The apparatus of claim 14, where said screen is a transparent window.

16. The apparatus of claim 14 where the screen includes a camera, an electronic display, and a processor where the processor is responsive to the image of the interior space created by said camera, and said processor presents information derived from said fluorescence of the at least one hand onto the electronic display.

17. The method of claim 14, further including the step of providing a processor that is responsive to the fluorescence of objects within said interior space.

18. The method of claim 17, where the processor includes a component that exchanges data pertaining to the fluorescence of objects within said interior space with one or more devices located remotely from said apparatus, and where the method includes the further step of exchanging said data between said component and said one or more devices.

19. The method of claim 18 further comprising the step of including the apparatus within a system to monitor the spread of bacterial contamination where said system includes least two of the apparatus at known locations, and the system monitors the spread in response to the fluorescence information exchanged by the at least two apparatus and their locations.

20. The method of claim 17 where said processor is programmed to determine whether said at least one hand is sufficiently bacteria free in response to said fluorescence; said method further comprising that said processor is operatively connected to a user indicator where said indicator is capable of signaling whether said hand is sufficiently bacteria free, based on criteria for whether said hand is sufficiently bacteria free; said method further comprising the steps of, after said ultraviolet light emitter emits ultraviolet light upon said hand:
 firstly, said processor determining whether said hand is sufficiently bacteria free; and
 secondly, said processor causing said indicator to signal whether said hand is sufficiently bacteria free.

21. The method of claim 20, said method further comprising preventing the spread of bacterial contamination via hands within the students and staff of a school, and visitors to said school, said method comprising the additional steps of:
 first, locating said apparatus within said school;
 second, causing one of said students, staff, or visitors to insert their at least one hand into said opening into said interior space,
 third, said processor determining whether said at least one hand is sufficiently bacteria free; and
 fourth, said processor causing said indicator to signal whether said at least one hand is sufficiently bacteria free.

22. The method of claim 20, said method further comprising one or more of the following:
 (a) preventing the spread of bacterial contamination via the hands of the persons employed by an establishment offering cosmetic services where said method comprises the additional steps of:
  first, locating said apparatus within an establishment offering cosmetic services;
  second requiring persons employed by said establishment offering cosmetic services to each insert one or more hands into said opening into said interior space, at specific times;
  third, said processor determining whether said hand is sufficiently bacteria free, based on criteria for whether said hand is sufficiently bacteria free;
  fourth, said processor causing said indicator to signal whether said hand has met said criteria for being sufficiently bacteria free; and
  fifth, requiring the owner of any hand that has not met said criteria for being sufficiently bacteria free to clean that hand;
 (b) preventing the spread of bacterial contamination via the hands of persons employed by a business where said method further comprising the steps of:
  first, locating said apparatus within a premises where said business operates;
  second, requiring persons employed by said business to each insert one or more hands into an opening into said interior space, at specific times;
  third, said processor determines whether said hand is sufficiently clean, based on criteria for whether said hand is sufficiently bacteria free;
  fourth, said processor causes said indicator to signal whether said hand has met said criteria to be sufficiently bacteria free; and
  fifth, requiring the owner of any hand that has not met said criteria for being sufficiently bacteria free to clean that hand;
 (c) preventing the spread of bacterial contamination via the hands of the persons employed by an establishment offering health care services where said method further comprising the steps of:
  first, locating said apparatus within said establishment offering health care services;
  second, said method further comprising requiring persons employed by said establishment offering health care services to insert on or more hands into an opening into said interior space;
  third, said processor determining whether said hand is sufficiently bacteria free, based on criteria for whether said hand is sufficiently bacteria free;
  fourth, said processor causing said indicator to signal whether said hand has met said criteria for being sufficiently bacteria free; and
  fifth, requiring the owner of any hand that has not met said criteria for being sufficiently bacteria free to clean that hand.

23. The method of claim 17, said method further comprising the steps of:
 first, providing multiple said apparatuses,
 second, providing that each said apparatus is operatively connected with at least one external processor that is external to that specific apparatus, in a manner which allows the processor within that specific apparatus to send data recorded by said processor to said external processor; and to send any other data said processor has received from processors in other said apparatuses to said external processor;
 third, providing that said external processor is capable of performing statistical calculations about the results of all said data recorded by said processors and transmitted directly or indirectly to said external processor, said statistical calculations including, but not limited to, the following:
  the mean and standard deviation of the percentage of the surface area of the hands that are contaminated by bacteria and have been inserted within a specific period of time into the interior spaces of the apparatuses from which said external processor has directly or indirectly received data;
  the differences between said mean and standard deviation during one period of time and said mean and standard deviation during a different period of time;
  the percentage of the hands that are contaminated by bacteria and that have been inserted, within a specific period of time, into the interior spaces of the apparatuses from which said external processor has directly or indirectly received data, the differences between said percentage during one period of time and said percentage during a different period of time,
 fourth, providing that said external processor creates a report of said statistical calculations.

24. A device for detecting pathogens contaminating the hand of a subject where the device includes:
 an ultraviolet pathogen detection light source;
 a means to project the ultraviolet pathogen detection light created by the ultraviolet pathogen detection light source onto the hand;
 a means to elicit a detectable reaction where the detectable reaction is responsive to the presence of pathogens on the hand and to the ultraviolet pathogen detection light;
 a screen by which the detectable reaction can be interpreted by the subject; and
 a means to self-clean portions of the device to eliminate pathogens contaminating those portions of the device.

25. The device of claim 24 where said detectable reaction is a visible reaction.

26. The device of claim 25 where said screen includes a transparent component through which the subject can view said visible reaction.

27. The device of claim 24 further including a communication component adapted to exchange information about said detectable reaction with a remote communication apparatus.

28. The device of claim 27 adapted into a system to monitor the spread of pathogen contamination where said system includes least two of the apparatus at known locations, and the system monitors the spread of pathogen contamination in response to the information concerning fluorescence of users' hands, transferred by the at least two apparatus, and to the locations of the at least two apparatus.

29. The device of claim 24 further comprising:
an enclosure into which said hand may be introduced through an opening into said enclosure with said ultraviolet pathogen detection light source adapted to project said ultraviolet pathogen detection light within the enclosure and onto the hand; and
a means to control the activation and inactivation of said ultraviolet pathogen detection light source in response to the hand being introduced into the enclosure.

30. The device of claim 29 where said means to control the activation and inactivation of said ultraviolet pathogen detection light source is responsive to sensors selected from the list comprising:
a) a light source whose light is blocked when said hand is introduced into said enclosure, and a sensor for detecting whether the light from said light source is blocked;
b) a sound source whose sound is blocked when said hand is introduced into said enclosure, and a sensor for detecting whether the sound from said sound source is blocked;
c) a voice detector;
d) a motion detector responsive the motion of said hand; and
e) a switch or button that is activated when said hand is introduced into said enclosure.

31. The device of claim 29 where said means to self-clean is a high intensity self-cleaning ultraviolet light adapted to bathe, with ultraviolet light, the interior surfaces of said enclosure where the intensity of the self-cleaning ultraviolet light is greater than the intensity of the ultraviolet pathogen detection light.

32. The device of claim 29 where said means to self-clean is a pathogen eliminating gas released within said enclosure.

33. The device of claim 32 where said pathogen eliminating gas is nitrogen dioxide.

34. The device of claim 32 where, prior to release of said pathogen eliminating gas, a mechanical screen is activated to cover all said openings into said enclosure to keep the pathogen eliminating gas from escaping said enclosure.

35. The device of claim 24 where said means to cause said detectable reaction is a sterile substance applied to said hand and distributed over the surface of the hand by the subject, and the substance produces the detectable reaction in response to the presence of both pathogens on the hand and said ultraviolet pathogen detection light.

36. The device of claim 24 where said device includes:
a camera adapted to image said detectable reaction;
a processor to receive data including the image adapted by the camera;
a computer program instructing the processor to inspect the data and evaluate the level of pathogen presence on the said hand; and
a display, visible to the subject and operatively connected to the processor, on which the processor informs the subject of the level of said pathogen presence on his hand.

37. A method for detecting pathogens contaminating the hand of a subject including the following steps:
a) providing a device having:
an ultraviolet pathogen detection light source and a means to project the ultraviolet pathogen detection light created by the ultraviolet pathogen detection light source onto the hand of the subject;
a means to elicit a detectable reaction where the detectable reaction is responsive to the presence of pathogens on the hand and to the ultraviolet pathogen detection light;
a screen responsive to, and capable of displaying, the detectable reaction;
a means to self-clean the device to eliminate pathogens contaminating the device; and
a means to activate the self-cleaning means in response to the detectable reaction;
b) arranging that the subject places the means of eliciting a detectable reaction onto the surface of his hand, and then places the hand into the path of the ultraviolet pathogen detection light to elicit the detectable reaction, and the subject detects pathogen contamination by interpreting the response to the detectable reaction displayed on the screen; and
c) activating the self-cleaning means in order to inactivate pathogens contaminating portions of the device after the user has withdrawn his or her hand from those portions of the device.

38. The method of claim 37 where step b) includes the steps of 1) activating and 2) inactivating the ultraviolet pathogen detection light source in response to the presence of said hand as detected by sensors selected from the list:
a) a light source whose light is blocked when said hand is introduced into said enclosure, and
b) a sensor for detecting whether the light from said light source is blocked;
c) a sound source whose sound is blocked when said hand is introduced into said enclosure, and a sensor for detecting whether the sound from said sound source is blocked;
d) a voice detector;
e) a motion detector responsive the motion of said hand; and
f) a switch or button that is activated when said hand is introduced into said enclosure.

39. The method of claim 37 where said detectable reaction is visible and said screen includes a transparent component through which the subject can view the visible reaction.

40. The method of claim 37 where providing a screen in step a) comprises the following steps:
providing a camera adapted to image said detectable reaction;
providing a processor to receive data including the image adapted by the camera;
providing a computer program instructing the processor to inspect the data and evaluate the level of pathogen presence on said hand; and
providing a display, visible to the subject and operatively connected to the processor, on which the processor informs the subject of the level of said pathogen presence on the hand.

41. The method of claim 37 where step a) further includes the step providing a communication component adapted to exchange, with a remote communication apparatus, information responsive to said detectable reaction.

42. The method of claim 41 further comprising the step of including the apparatus within a system to monitor the spread of pathogen contamination where said system includes least two of the apparatus at known locations, and the system monitors the spread in response to the fluorescence information exchanged by the at least two apparatus and their locations.

43. The method of claim 37 where step a) further comprises the steps:
- providing an enclosure into which said hand may be introduced through an opening with said ultraviolet pathogen detection light source adapted to project said ultraviolet pathogen detection light within the enclosure and onto the hand; and
- providing a means to control the activation and inactivation of said ultraviolet pathogen detection light source in response to the hand being introduced into the enclosure.

44. The method of claim 43 where said self-cleaning means is a high intensity self-cleaning ultraviolet light source adapted to bathe the interior surfaces of said enclosure where the intensity of said self-cleaning ultraviolet light is greater than the intensity of said ultraviolet pathogen detection light.

45. The method of claim 43 where said self-cleaning means is a pathogen eliminating gas released within said enclosure.

* * * * *